US012544178B2

(12) United States Patent
Squicciarini

(10) Patent No.: US 12,544,178 B2
(45) Date of Patent: Feb. 10, 2026

(54) HAND-HELD PUPILOMETER DEVICE WITH STOWABLE BREATH SHIELD

(71) Applicant: OptiSource International, Inc., Bellport, NY (US)

(72) Inventor: Daryl Squicciarini, Bellport, NY (US)

(73) Assignee: OptiSource International, Inc., Bellport, NY (US)

(*) Notice: Subject to any disclaimer, the term of this patent is extended or adjusted under 35 U.S.C. 154(b) by 495 days.

(21) Appl. No.: 17/818,642

(22) Filed: Aug. 9, 2022

(65) Prior Publication Data

US 2023/0045243 A1 Feb. 9, 2023

Related U.S. Application Data

(60) Provisional application No. 63/231,122, filed on Aug. 9, 2021.

(51) Int. Cl.
*A61B 90/00* (2016.01)
*A61B 3/11* (2006.01)

(52) U.S. Cl.
CPC ................ *A61B 90/05* (2016.02); *A61B 3/11* (2013.01)

(58) Field of Classification Search
CPC ................................. A61B 90/05; A61B 3/11
USPC .......................................................... 351/204
See application file for complete search history.

(56) References Cited

U.S. PATENT DOCUMENTS 7,003,802 B2 * 2/2006 Broersma .............. A63B 71/10 2/427
2014/0268037 A1 * 9/2014 Siminou .............. A61B 3/0083 351/205
2018/0279948 A1 * 10/2018 Medberry ............ A61B 5/4064
2021/0337887 A1 * 11/2021 Johnson ................. A41D 13/11

* cited by examiner

*Primary Examiner* — Sharrief I Broome
(74) *Attorney, Agent, or Firm* — BOOTH ALBANESI SCHROEDER PLLC; Peter V. Schroeder

(57) ABSTRACT

A hand-held pupilometer device is held between the practitioner and a patient and used to view the eye or eyes of the patient. The pupilometer includes a stowable breath shield which can be moved from a stowed position and an engaged position. In the engaged position, the breath shield is positioned between the practitioner and the patient.

10 Claims, 3 Drawing Sheets

HAND-HELD PUPILOMETER DEVICE WITH STOWABLE BREATH SHIELD

CROSS-REFERENCE TO RELATED APPLICATIONS

This is a U.S. Non-Provisional application for Patent claiming priority to U.S. Provisional Patent Application No. 63/231,122, filed Aug. 9, 2021, entitled Hand-held Pupilometer Device with Breath Shield.

TECHNICAL FIELD

The disclosure relates to an pupilometer device, a pupilometer, and more particularly, to a hand-held pupilometer device having a breath shield movably mounted thereon.

BRIEF DESCRIPTION OF THE DRAWINGS

For a more complete understanding of the present disclosure, and the advantages thereof, reference is now made to the following description which is to be taken in conjunction with the accompanying drawings in which like reference numerals indicate like parts and wherein.

DETAILED DESCRIPTION OF THE DISCLOSURE

Hand-held pupilometer devices are of small size, designed to be held in the hand of the optical examiner. The pupilometer device is generally held in front of the face of the person being examined, the patient. The device typically has a viewing frame, often with one or more lenses, apertures, and the like, and is for viewing the eye or eyes of the patient. The pupilometer device is held, in use, at a relatively close proximity to the face of the patient and at a relatively close proximity to the face of the device user. The hand-held pupilometer devices discussed herein are exemplary and non-limiting.

The relative proximity of the user's and patient's faces, obviously, creates a danger for transmission respiratory particles, and any viruses, bacteria, or other foreign objects, carried in the respiratory particles. Infection during pupilometers has become a more critical issues, especially since the advent of the COVID-19 virus.

Consequently, in the embodiments of the disclosure herein, a breath shield is provided to block transmission of respiratory particles between the user and patient. The exemplary breath shields shown and discussed are movably attached to the pupilometer device. The movable shields can be slidably, hingedly, or pivotally attached to the device.

Figure 1:
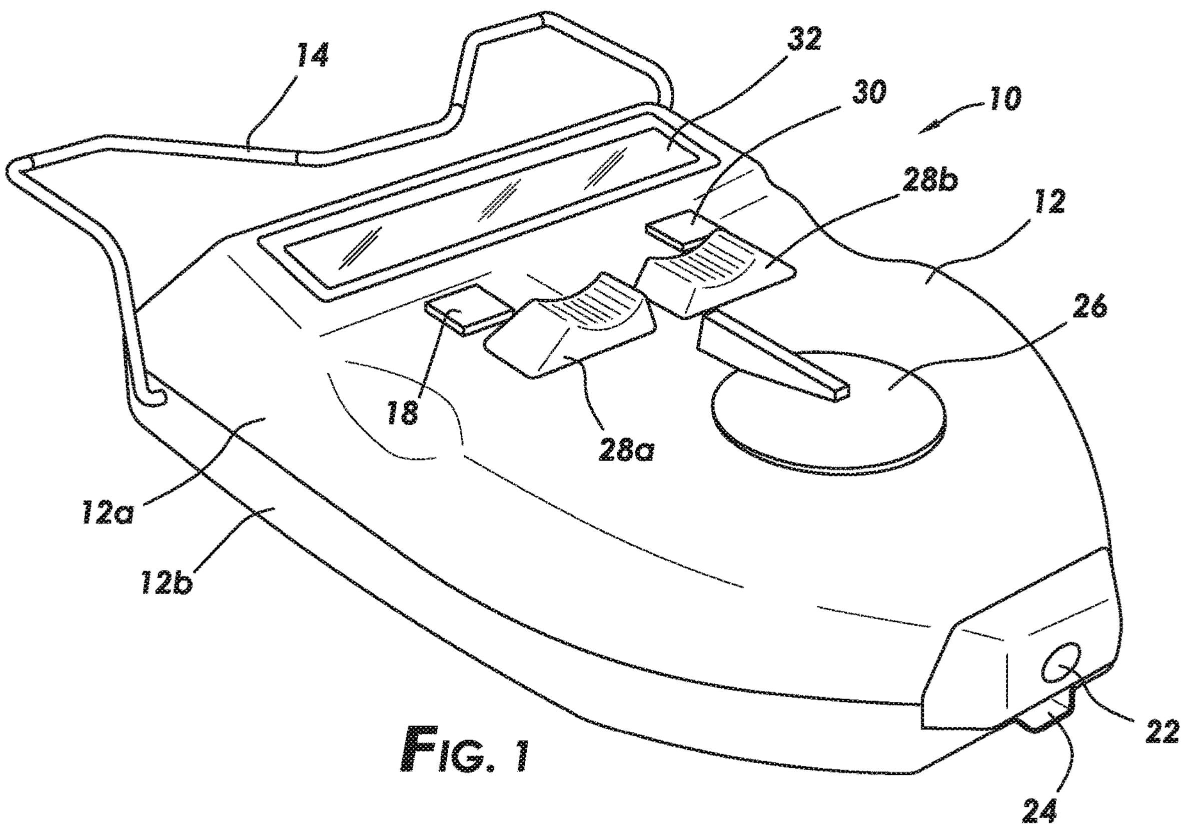
FIG. 1 is an orthogonal view of an exemplary hand-held pupilometer device having a breath shield according to certain aspect of the disclosure.
Figure 2:
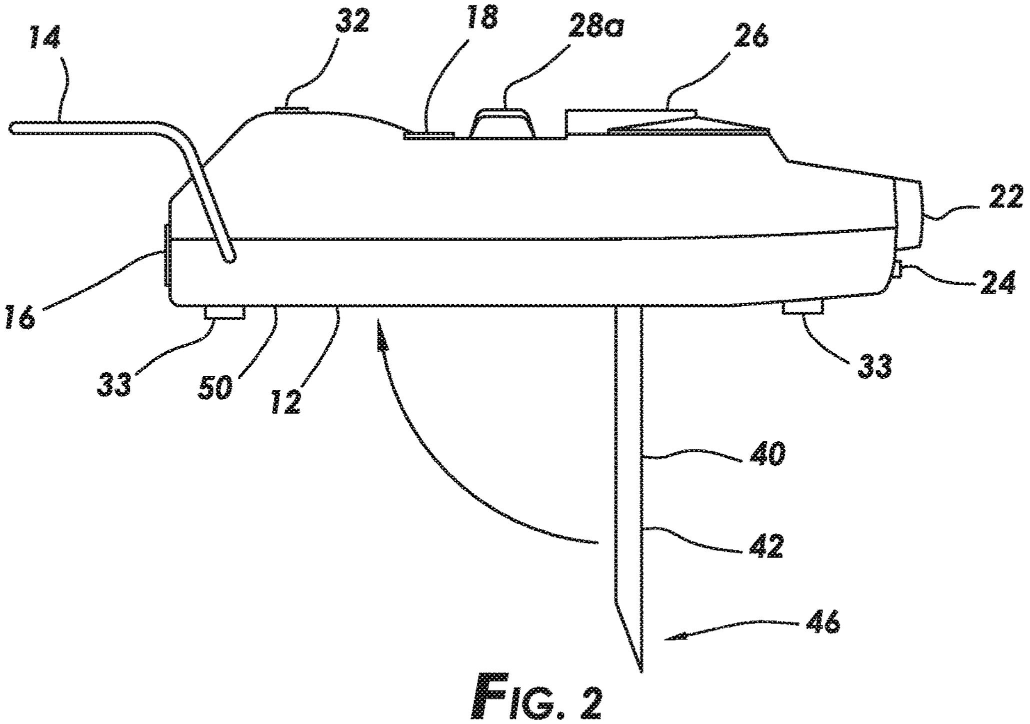
FIG. 2 is a side view of the device of FIG. 1, showing an exemplary breath shield in an extended position.
Figure 3:
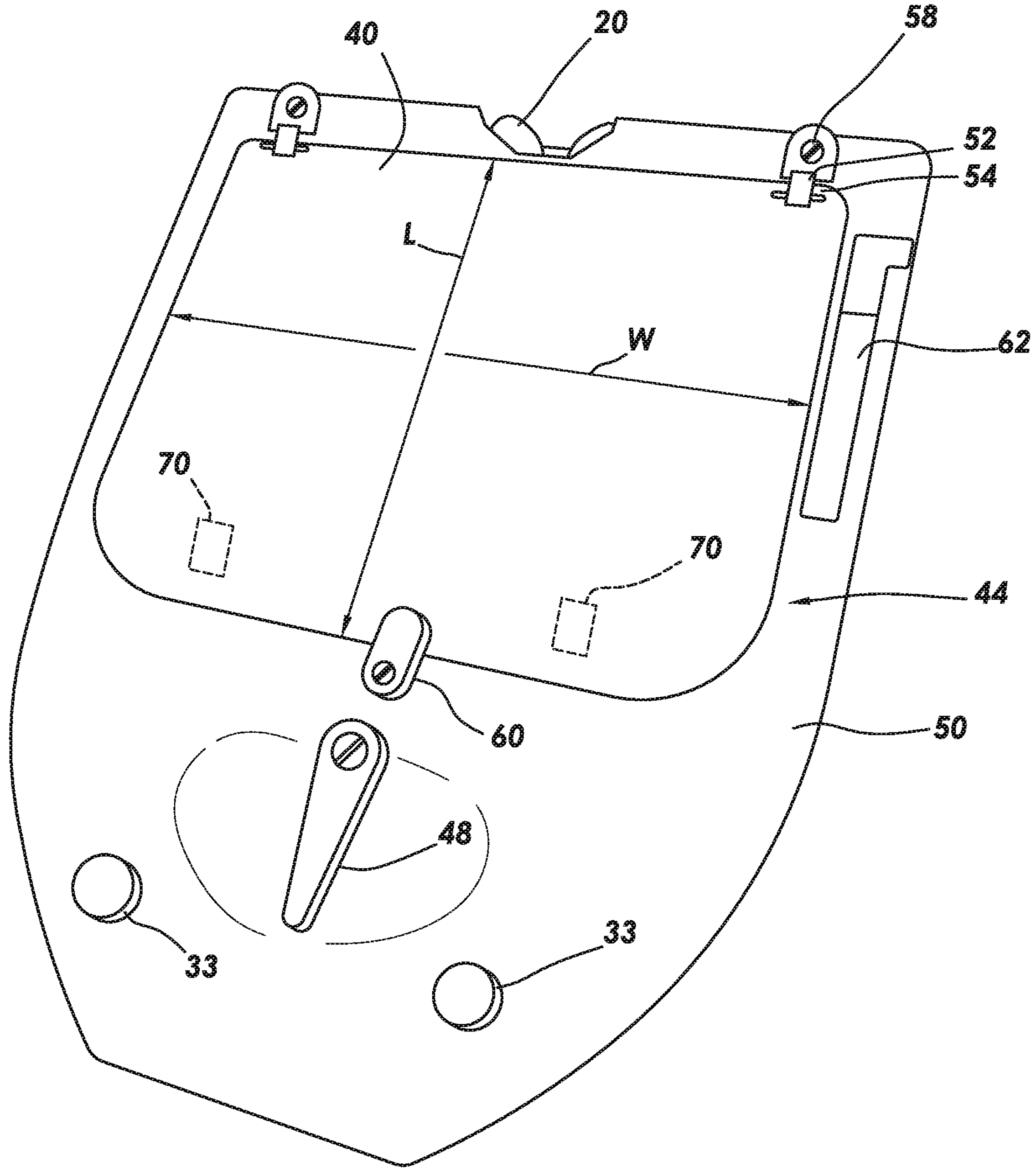
FIG. 3 is a bottom view of the device of FIGS. 1-2 showing an exemplary breath shield in a stored position.
Figure 4:
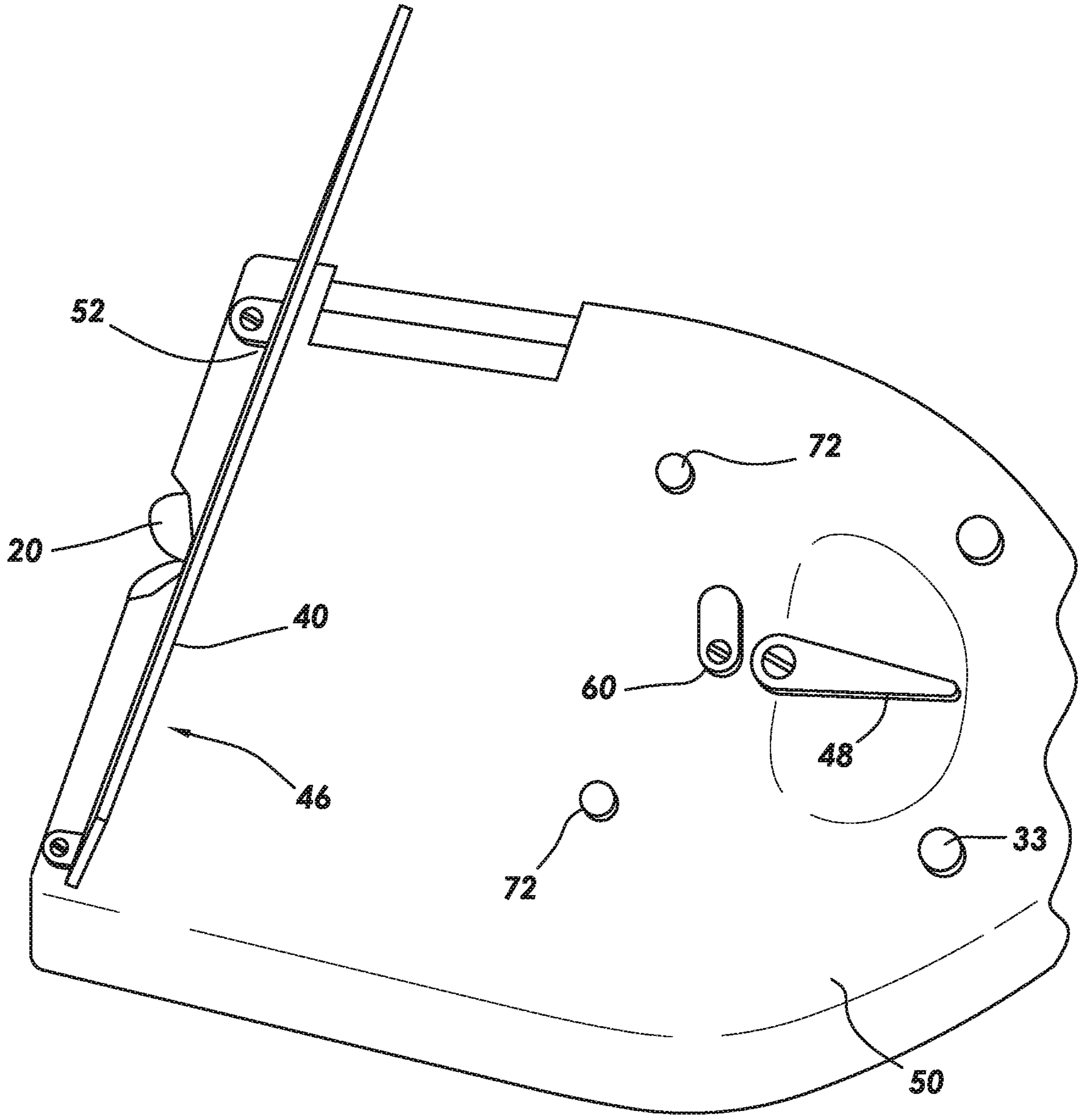
FIG. 4 is a bottom view of the device of FIGS. 1-3 showing the breath shield in an extended position.

FIG. 1 is an orthogonal view of an exemplary hand-held pupilometer device having a breath shield according to certain aspect of the disclosure. FIG. 2 is a side view of the device of FIG. 1, showing an exemplary breath shield in an extended position. FIG. 3 is a bottom view of the device of FIGS. 1-2 showing an exemplary breath shield in a stored position. FIG. 4 is a bottom view of the device of FIGS. 1-3 showing the breath shield in an extended position. The Figures will be discussed together, with like numbers used to refer to like parts. The embodiment seen in the Figures is merely exemplary and not limiting.

The Figures show an exemplary hand-held pupilometer device, namely, a hand-held pupilometer, or PD Meter. The hand-held pupilometer device 10 comprises a body 12 housing working parts of the device. For example, the body 12 can house pupilometer equipment, such as electronics, computer and computerized equipment, batteries, optical lenses and devices, measuring devices, sensors, etc., for examination of the patient's eye or eyes. The equipment can be housed in an interior space of the device body. The pupilometer device may be designed for use in contact with the patient's face or in contact with the user's face. The pupilometer device may have movable parts, such as folding, pivoting, or sliding members serving to position working parts or maintain spaced relationships.

The exemplary hand-held optical device 10 is a pupilometer and includes a body 12 for housing the working parts of the device, such as lenses, computerized parts and the like, not shown. The body 12 can be monolithic or defined by, for example, upper and lower housings 12*a-b*. The pupilometer device 10 has a forehead rest bar 14, observation windows 16, an on/off button 18, a nose rest 20, a view finder 22, a compensating ocular key 24, a viewing distance adjustment mechanism 26, left and right eye monocular adjustment levers 28*a-b*, a control or operational key 30 (for example, to switch between pupillary and visual distance functions), a monocular covering knob 48, and feet 32. The various control knobs and buttons are mounted on the pupilometer device body 12, movably as necessary for operation. Parts can be removable and replaceable as desired, such as nose rest covers, forehead rest covers, and for part repair and replacement. The pupilometer device can be battery powered and have an internal compartment 62 for a power source. The pupilometer device body 12 can include detents, apertures, flanges and the like to cooperate with other device parts. A display window 32 is provided for displaying information related to the examination or results thereof, such as left, right and binocular PD, etc. The operation and parts of pupilometers are understood in the art and are not described in detail herein.

A breath shield 40 is provided to block, prevent, or deflect transmission of respiratory particles between a user of the pupilometer and a patient. The breath shield 40 generally comprises a generally solid plate 42 through which air and airborne particles cannot pass. The shield 40 can take any desired physical shape which may depend on the shape and size of the device, although the exemplary embodiment shown provides a generally planar shield having a width, W, approximately that of the device. The shield has a length, L, such that, when the shield is in the engaged position 46, the shield 40 is positioned to extend from the device in a direction and over a distance to effectively block transmission of respiratory particles exhaled from the mouth and nose of either the user, patient or both. The shield can be made of any suitable material, for example, plastic, metal, rubber, etc.

The shield is movable between a stowed position 44 and an engaged position 46. In the stowed position 44, seen in FIGS. 1 and 3, the shield 40 is disposed flush with or countersunk into the device body 12. In the embodiment shown, the breath shield is attached to and extends from the lower surface 50 of the device. In other embodiments, the shield can be attached to and/or extend from the upper surface or a side surface of the pupilometer device. The shield 40 can pivot, slide, or otherwise move in relation to the pupilometer body 12. The shield can be movably attached to the pupilometer body 12 by one or more hinges, such as pivot hinges, butt hinges, concealed hinges, barrel hinges, overlay hinges, offset hinges, piano hinges, strap hinges, and the like, or by cooperating slidable rails, articulated joints, swivels, and the like.

In the embodiment shown, the shield 40 is a generally flat plate 42 pivotally attached to the pupilometer device body 12. The shield 40 is attached to the body 12 by multiple hinges 50 comprising cooperating hinge mechanisms 52 and 54, such as barrel and pin, pin and knuckle, pin and groove, etc., as is known in the art. The cooperating hinge mechanisms can be formed monolithically with the shield 40 and body 12, or can be attached thereto. For example, the shown shield has hinge mechanisms 54, namely, pins, defined by the shield plate, while the hinge mechanisms 52 define cooperating knuckles, grooves or sockets extending from posts 56 which are threadedly attached to the body at fasteners 58. The cooperating hinge mechanisms can attach to one another by friction fit, snap-on fit, or by other fastening mechanisms known in the art.

The shield 40 is attached to or defines one or more hinge members which cooperate with and attach to corresponding hinge members defined on or attached to the pupilometer device. For example, hinge knuckles and pins can constitute the hinge members. Hinge plates or leaves can be attached to the breath shield and/or pupilometer device body. Alternately, the breath shield and pupilometer device body can serve as integrally formed hinge leaves. The breath shield can hingedly or pivotally attach to the pupilometer device by friction fit, snap-together fit or other fits as is known in the art. Hinge types and designs are known in the art.

The breath shield 40, in an embodiment, folds to a stowed configuration 46 in which the shield 40 is flush to a generally flat surface of the pupilometer device body 12. The shield 40 can stow into a countersunk position, such as where the pupilometer body 12 provides a shaped detent or indentation for that purpose.

The breath shield 40 can be attached to the device body 12 at almost any location. For example, in FIGS. 1-2, the breath shield 40 is hingedly attached to the pupilometer body adjacent the patient's end of the device, near the observation windows 16. In such an arrangement, the shield, when in the engaged position, is closer to the mouth and nose of the patient. Alternately, the breath shield 40 can be hingedly attached adjacent the user's end of the device, as seen in FIGS. 3-4.

In the stowed position, the shield can be releasably held in position by a selective locking mechanism 60. The locking mechanism 60 can be user operated and selective, such as a pivoting latch, lock or the like. Alternatively, the locking mechanism 60 can comprise a releasable friction fit or snap-on connection, such as by cooperating interlocking components, such as hoop-strain, cantilevered, or other snap-fit components. Alternately, the shield 40 may house one or more magnets 70 which cooperate with similar magnets 72 mounted in the device body 12, such that when in the stowed position the magnets maintain the shield in position.

Similarly, in the engaged position 44, the shield can be releasably held in position by such locking mechanisms such that the shield stays in the engaged position once moved by the user, and maintains that position until moved away from the engaged position by the user.

The breath shield can be biased towards the stowed position, such as by a biasing spring or the like, as is known in the art.

In an embodiment, the breath shield is slidably attached to the hand-held pupilometer device. The shield and device body, for example, can define cooperating tongues and grooves.

While the making and using of various embodiments of the present disclosure are discussed in detail below, it is appreciated that the present disclosure provides many applicable concepts that may be embodied in a wide variety of specific contexts. The specific embodiments discussed herein are merely illustrative of specific ways to make and use the disclosure. Only the claims appended hereto delimit the scope of any claimed inventions.

The invention claimed is:

1. An pupilometer device comprising:

a hand-held pupilometer device body for grasping by a user in examining a patient's eye or eyes;

pupilometer optical equipment for examination of the patients' eye or eyes housed within an interior of the pupilometer device body;

a breath shield movably attached to the pupilometer device body, the breath shield movable between an engaged position, wherein the breath shield is positioned to block transmission of respiratory particles between the user and the patient, and a stowed position, wherein the breath shield is stowed on or in the device and does not block the movement of respiratory particles between the user and the patient;

the breath shield selectively and releasably held in the stowed position by a first locking mechanism; and the breath shield selectively and releasably held in the engaged position by a second locking mechanism.

2. The pupilometer device of claim 1, wherein the breath shield is a generally rigid plate hingedly connected to the device body.

3. The pupilometer device of claim 2, wherein the breath shield and the device body further comprise cooperating hinge mechanisms, and wherein the cooperating hinge mechanisms are attachable by friction fit or snap-on connections.

4. The pupilometer device of claim 1, wherein the breath shield is pivotally or slidably movable with respect to the device body.

5. The pupilometer device of claim 1, further comprising a second breath shield movably attached to the device body.

6. The pupilometer device of claim 1, further comprising a first locking mechanism for releasably maintaining the breath shield in the stowed position.

7. The pupilometer device of claim 6, further comprising a second locking mechanism for releasably maintaining the breath shield in the engaged position.

8. The pupilometer device of claim 7, wherein at least one of the first and second locking mechanisms is a friction fit or snap-on attachment.

9. The pupilometer device of claim 6, wherein the first locking mechanism comprises cooperating magnets positioned on the breath shield and the device body.

10. The pupilometer device of claim 1, wherein breath shield is biased towards the stowed position.

* * * * *